United States Patent [19]

Zelman

[11] Patent Number: 5,057,098
[45] Date of Patent: Oct. 15, 1991

[54] APPARATUS AND METHOD FOR EXTRACTING CATARACT TISSUE

[75] Inventor: Jerry Zelman, Miami Beach, Fla.

[73] Assignee: Ophthalmocare, Inc., Los Gatos, Calif.

[21] Appl. No.: 245,144

[22] Filed: Sep. 16, 1988

Related U.S. Application Data

[63] Continuation-in-part of Ser. No. 44,544, May 1, 1987, Pat. No. 4,825,865.

[51] Int. Cl.$^5$ .............................................. A61B 17/00
[52] U.S. Cl. ...................................... 606/6; 606/107; 604/22; 604/27; 604/28; 604/266
[58] Field of Search ............... 128/303.1, 395; 604/20, 604/22, 27, 28, 30, 35, 266–268, 902; 606/6, 14, 107

[56] References Cited

U.S. PATENT DOCUMENTS

| | | | |
|---|---|---|---|
| 1,112,982 | 10/1914 | Conine | 604/267 |
| 2,137,635 | 11/1938 | Tyler | 604/267 |
| 3,589,363 | 6/1971 | Banko | 604/27 |
| 3,693,613 | 9/1972 | Kelman | 604/22 |
| 3,930,505 | 1/1976 | Wallach | 604/28 |
| 3,942,519 | 3/1976 | Shock | 128/303.1 |
| 3,982,541 | 9/1976 | L'Esperance | 604/20 |
| 3,996,935 | 12/1976 | Banko | 604/28 |
| 4,011,869 | 3/1977 | Seiler, Jr. | 604/267 |
| 4,223,676 | 9/1980 | Wuchinich | 604/22 |
| 4,520,816 | 6/1985 | Schachan et al. | 128/303.1 |
| 4,522,206 | 6/1985 | Whipple et al. | 128/305 |
| 4,633,866 | 1/1987 | Peyman et al. | 128/303.1 |
| 4,694,828 | 9/1987 | Eichenbaum | 128/303.1 |

FOREIGN PATENT DOCUMENTS 175096 3/1986 European Pat. Off. ............... 604/33

Primary Examiner—David Shay
Attorney, Agent, or Firm—Cushman, Darby & Cushman

[57] ABSTRACT

Apparatus and method for extracting cataract tissue in which the cataract is first softened by focusing laser radiation thereon and subsequently a tube inserted through an incision to a position adjacent the cataract. An irrigating liquid is supplied through one portion of the tube and the liquid and cataract fragments removed via an aspiration opening adjacent the tube opening. Fragments which do not readily pass through the aspiration opening are dislodged by vibration or broken up by a paddle like member pivotally mounted adjacent the aspirating opening to engage the fragment and apply a force to break up the same. The tube has a shovel shaped tip which facilitates separation of fragments from the cataract body and facilitates location of the same adjacent the aspiration opening.

22 Claims, 2 Drawing Sheets

APPARATUS AND METHOD FOR EXTRACTING CATARACT TISSUE

This is a continuation-in-part of my earlier application Ser. No. 07/044,544, filed May 1, 1987, now U.S. Pat. No. 4,825,865.

BACKGROUND OF THE INVENTION

The present invention relates to an apparatus and method for extracting cataract tissue and, in particular, to a shovel or scoop tipped probe for extracting cataract tissue.

Every eye is divided into an anterior and posterior chamber by a normally transparent lens which focuses light onto the retina at the back of the posterior chamber. When the lens becomes cloudy for any of a variety of reasons, sight is impaired and the cloudy lens must be removed. Following removal of the lens, an intraocular lens (IOL) implant can be placed in the posterior chamber or thick glasses or contact lenses used to focus the light properly onto the retina.

A number of techniques are now in use for removing the cloudy cataract lens. In all these techniques a surgical tool is inserted into the eye through a small incision. Phacoemulsification is a recently developed technique which is being used more and more frequently. A small incision is made in the surface of the eye and a probe in the form of a rigid or semi-rigid tube inserted. This tube defines two internal paths—one for supplying an aspirating liquid, typically water, to the interior of the eye and a second to which a vacuum is connected for sucking out fragments of the cataract tissue and the aspirating liquid. Ultrasonic vibration is applied to the tube after the sharpened end is inserted by the surgeon into the cataract tissue. The ultrasonic vibration breaks up the cataract tissue which is aspirated together with the irrigating liquid.

One advantage of phacoemulsification is that the incision in the eye can be smaller than with other techniques. A smaller incision stabilizes the refractive error sooner and reduces the amount of induced post operative astigmatism. Of course that advantage is lost if the incision must be lengthened to insert the IOL. However, the present development of small incision intraocular lenses and the future possibility of in sito formation of lenses by injection of polymer into the intact capsular bag make phacoemulsification particularly attractive since with these techniques the incision need not be increased beyond the initial 2.5-3.5 millimeters required for phacoemulsification.

One difficulty with phacoemulsification is that considerable problems are often encountered in mastering the skills needed to perform the procedure safely. Further, occasional difficulties arise in removing all of the cataract tissue In addition the sharp point of the probe can inadvertently damage delicate eye tissues.

Laser radiation has for the past several years been used to ablate various tissues within the eye. For example, the use of a ND:YAG laser (hereinafter referred to by the more common term, YAG laser) to remove abnormal and normal tissue has been explored, for example, see the patent to Krasnov, U.S. Pat. No. 3,971,382; U.S. application Ser. No. 702,569 filed Feb. 19, 1985; and an article by William Steven Chambles entitled *Neodymium: YAG Laser Anterior Capsulotomy And A Possible New Application,* (AM Intra-Ocular Implant Society Journal, Vol. 11, January 1985). It has generally been recognized that laser radiation, particularly from a YAG laser, will soften cataract tissue.

However, one of the difficulties with the use of laser radiation to soften cataract tissue is that the fragments of the tissue are often too large or otherwise not dimensioned to pass readily through an aspirating opening in a probe such as used in phacoemulsification. In order to avoid making the incision more than the desired 2.5-3.5 millimeters, the aspirating opening must necessarily be quite small and the dimensions of the part within the probe to the vacuum source similarly restricted. For that and other reasons, the use of laser radiation to soften cataract of subsequent aspiration has not been practical as a standard surgical procedure.

My earlier application Ser. No. 07/044,544 relates, generally, to an apparatus and method practical the use of laser radiation to soften and eventually fragment cataract tissue which can then be removed through an instrument inserted through a 2.5-3.5 millimeter incision in the surface of the eye. According to that invention, fragments which do not pass readily through the aspirating opening are dislodged.

In a first embodiment of my earlier invention, this is accomplished by providing some vibration of the instrument, for example, akin to the ultrasonic vibration which is provided during conventional phacoemulsification. The vibration may to some extent cause further fragmentation and also causes the fragment to move until it is positioned so it can pass through the aspirating opening.

According to a second embodiment of my earlier invention, a paddle like member is pivotally mounted adjacent to the aspiration opening and biased to a position lying against the tube surface. Fragments which are lodged in the opening can be easily broken up by pivoting the paddle like member toward the opening, engaging the fragment and applying a force to the same which results in it being broken up. The smaller fragments resulting are then sucked through the aspirating opening. In this fashion, the fragments can be readily and easily removed from the eye.

The probe tube of my earlier invention is further provided with an interior portion for supplying aspirating liquid, preferably water, through the end thereof and a sleeve extending about that portion having an aspirating opening adjacent the end thereof. The end of the probe tube of my earlier invention was rounded so as to reducing the potential for damage to other tissue inherent in conventional phacoemulsification.

SUMMARY OF THE INVENTION

The present invention constitutes a modification of my earlier probe tube and in particular a modification of the shape of the probe tube tip. More particularly, the probe tube provided in a accordance with the present invention has a sloped, shovel-like tip. Indeed, I have found that with the round tip probe tube of my earlier invention it can be difficult at times to dislodge fragments of cataract from the main body of the cataract so that the fragments are disposed adjacent the aspiration opening so that in particular the member for applying a force to the fragment can effectively contact the cataract fragments. The provision of a sloped shovel-type tip advantageously permits fragments to be dislodged from the main body of the cataract and easily positioned adjacent the aspiration opening thereby facilitating breaking up of the fragment, in particular by a paddle-like member provided in accordance with the preferred embodiment of the present invention.

Other objects, features and characteristics of the present invention, as well as the methods of operation and functions of the related elements of the structure, and the combination of parts and economies of the manufacture will become more apparent upon consideration of the following detailed description and the appended claims with reference to the accompanying drawings all of which form a part of this specification, wherein like reference numerals designate corresponding parts in the various figures.

DETAILED DESCRIPTION OF THE PREFERRED EMBODIMENT

Figure 1:
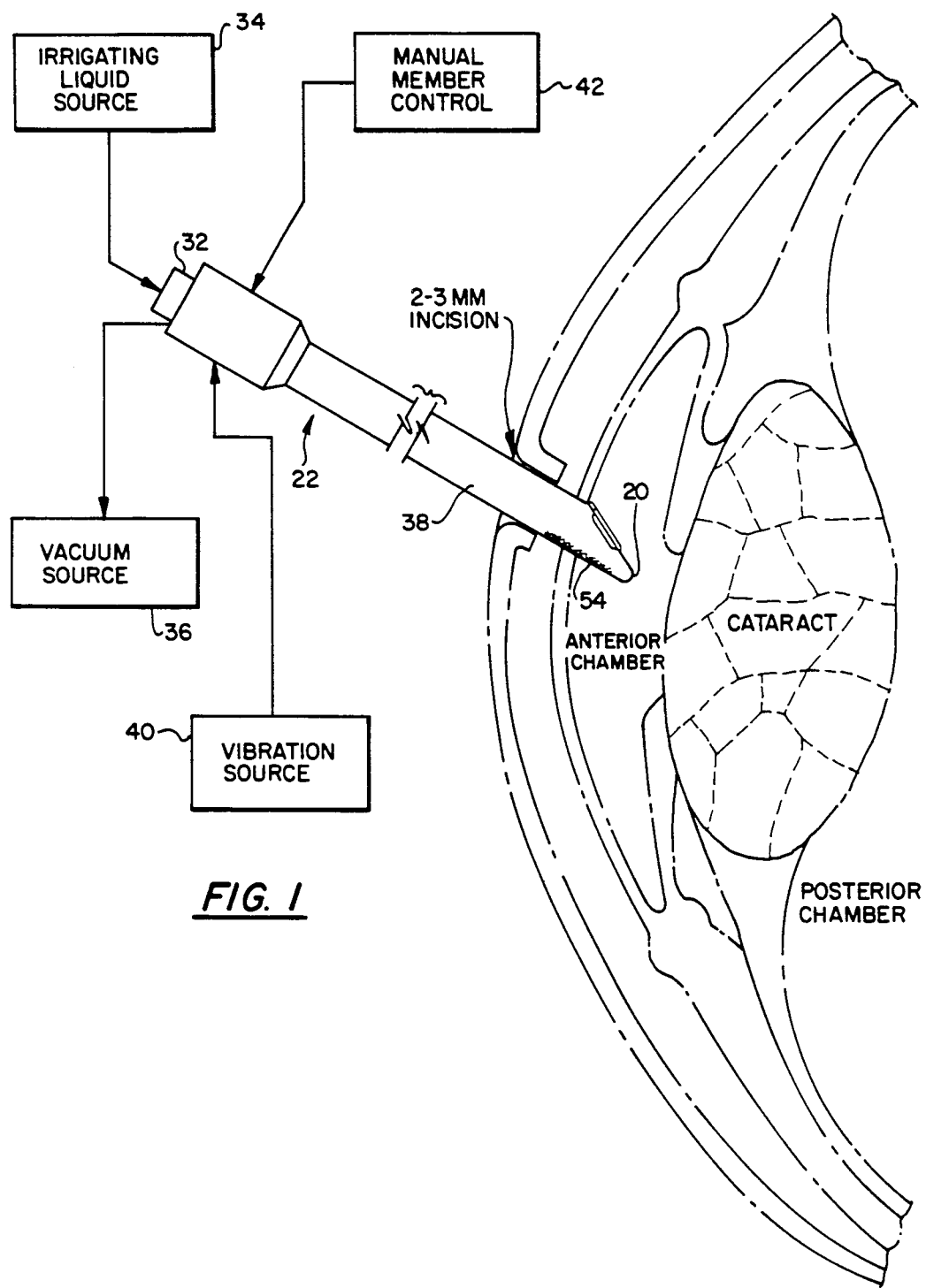
FIG. 1 shows a schematic view of the tissue extracting apparatus of the present invention in place within a schematically illustrated eye for removing cataract tissue.

Reference is now made to FIG. 1 which illustrates a first embodiment of the invention. The shovel or scooped end 20 of a probe tube 22 shown only partially in FIG. 1 has been inserted through a 2.5–3.5 millimeter incision conventionally made in the surface of the eye at an appropriate location. The end 20 of tube 22 is then manipulated adjacent cataract tissue softened and substantially fragmented by the previous application of laser radiation.

Figure 4:
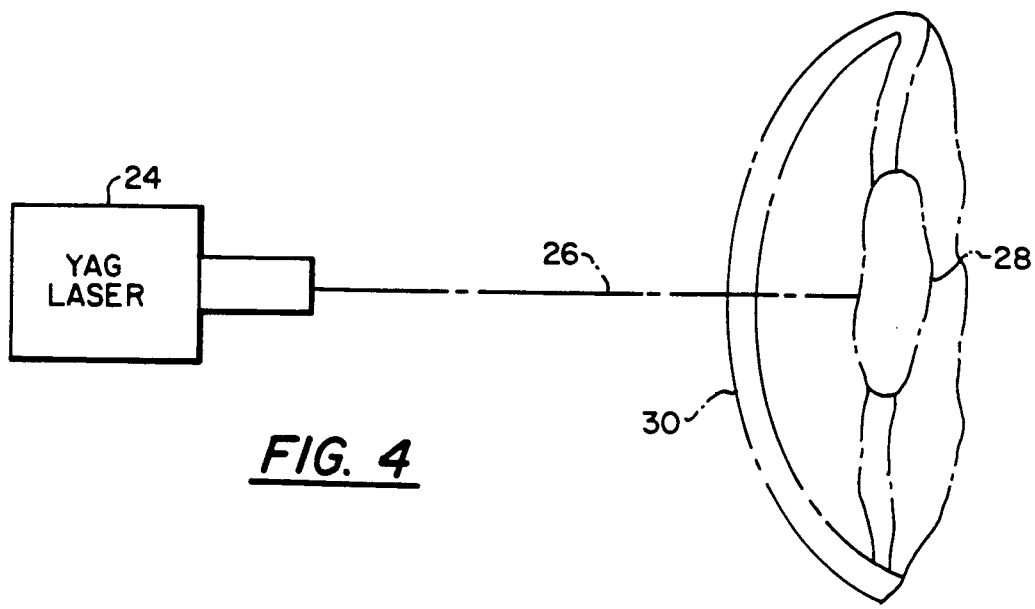
FIG. 4 shows a schematic view of the application of laser radiation from a YAG laser to soften the cataract tissue.

FIG. 4 shows a laser 24 schematically applying a beam of radiation 26 to a clouded lens 28 in a schematically illustrated eye 30. A conventional YAG laser using burst of three mJ to five mJ focused on the center of the nucleus has been shown to produce satisfactory softening. At least 50 laser bursts are first applied to the posterior aspect of the nucleus at 3 mJ. Another 100–150 shots of 5–7 mJ are then applied to the center of the nucleus. Considerable time, a week or more, may pass between softening and removal.

Referring again to FIG. 1, irrigating liquid is supplied to the interior portion 32 of a rigid or semi-rigid tube 22 from a schematically illustrated irrigating liquid source 34. Tube 22 forms part of a probe which includes a handpiece (not shown) manipulated by the surgeon. The handpiece is essentially the same as a conventional phacoemulsification device. Normally the irrigating liquid is sterile water. Vacuum from a suitable source 36 is similarly applied to a second portion 38 of tube 22 which is in the form of a sleeve extending about portion 32. Vibration source 40 and the manual control member 42 are also connected to tube 22. These various elements and sources can be arranged in much the same fashion as with conventional phacoemulsification devices available today.

Figure 2:
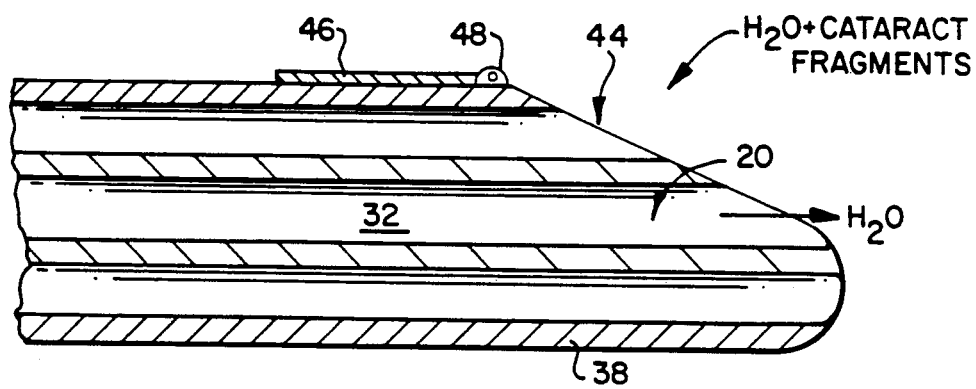
FIG. 2 shows a detailed view of the end of the tube of FIG. 1 showing the shovel tip and the paddle-like member overlying the aspirating opening.
Figure 3:
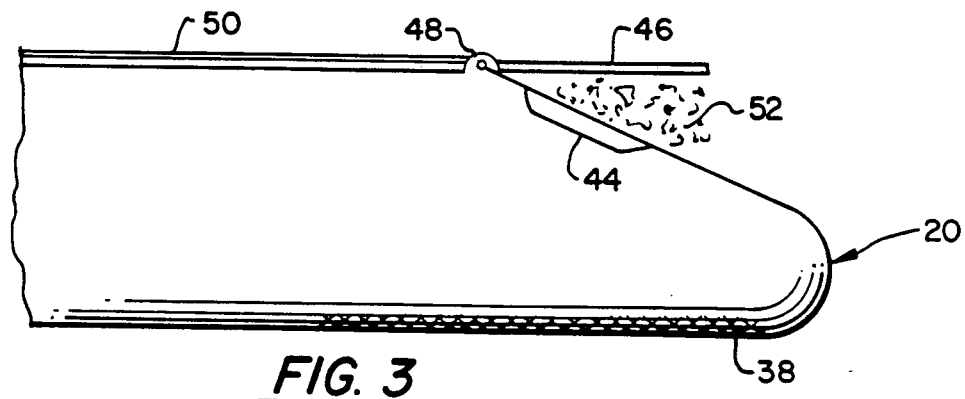
FIG. 3 shows a further schematic view illustrating a fragment of cataract tissue being broken up by a paddle like member.

FIGS. 2 and 3 show, in greater detail, the arrangement of the scoop end 20 of the embodiment. As can be seen in FIG. 2, aspirating opening 44 is provided in the sloped wall of tube 22 adjacent end 20. Aspirating liquid and cataract fragments are sucked through this opening into sleeve 38 and eventually returned to the vacuum source 36.

The scoop end 20 is used to dislodge fragments of the cataract from the main body of the cataract. This allows one to place this fragments over the aspiration port or opening 44. In order to dislodge fragments which do not readily pass through this opening, vibration is applied at an intensity and for a time until the surgeon observes the aspirating opening is no longer blocked.

In addition to, or as an alternative, paddle like member 46 can be pivotally mounted at a pivot 48 adjacent the aspirating opening. Paddle like member 46 is normally biased into the position illustrated in FIG. 2, lying along the exterior surface of tube 22 during insertion of the instrument into the eye. From time to time fragments will become lodged in the aspiration opening, as shown in FIG. 3. Those fragments may potentially be dislodged by use of vibrations or alternatively may be broken up by use of the paddle like member. To do that, the paddle like member is simply moved by the manual control member, for example with a cable or rod 50, downward to engage the fragment 52, for example, and apply a force to the same, crushing the fragment between the sloped surface of the tube 22 adjacent the opening and paddle like member 46. The shovel or scoop shape facilitates location of the fragments at the aspiration opening and thus ensures that the paddle will be able to apply a force to the fragment and that the fragment will break up and will enter the aspiration opening. Very little force is, in fact, required to break up the very tiny and fragile fragments of tissue which are produced by the laser radiation. Once the fragment has been broken up, paddle like member 46 can be returned to its opening position, for example with cable or rod 50 and the removal of the cataract tissue continued.

It is also conventional in this type of operation to polish the posterior capsule after removal of the clouded natural lens in order to make sure that all excessive cells are removed. It is convenient to provide a roughened portion 21 as shown in FIG. 1 on part of the wall of the tube 20 adjacent end 22 for the purpose.

While the invention has been described in connection with what are presently considered to be the most practical and preferred embodiments, it is to be understood that the invention is not limited to the disclosed embodiments, but, on the contrary, it is intended to cover various modifications and equivalent arrangements included within the spirit and scope of the appended claims.

What is claimed is:

1. An apparatus for extracting fragments of cataract tissue comprising:

a probe adapted for insertion into the eye through an incision for supplying an irrigating liquid to the interior of said eye through an irrigation opening and aspirating that liquid and fragments of cataract tissue through an aspiration opening, said probe having a distal insertion end and a proximal end, said distal end being shovel shaped so as to have a blunt distalmost end and a distal side face sloping from a maximum dimension to a minimum dimension at the blunt distalmost end, said aspiration opening and said irrigation opening being defined through said sloped side face; and means for dislodging fragments of cataract tissue at said aspiration opening which have not passed through said aspiration opening.

2. An apparatus as in claim 1 wherein said means for dislodging fragments includes means for vibrating said probe.

3. An apparatus as in claim 1 wherein a portion of a wall of said probe adjacent said distal end and opposite to said sloped side face is roughened for polishing a posterior capsule of the eye.

4. An apparatus as in claim 1 wherein said probe has an inner portion opening at the distal end for supplying said liquid and an outer sleeve extending about said inner portion and having at least one said aspirating opening in a wall thereof adjacent to said distal end.

5. An apparatus as in claim 1 further including means for supplying said liquid to a first portion of said probe and means for applying a vacuum to a second portion of said tube for aspiration.

6. An apparatus as in claim 1 wherein said means for dislodging fragments includes a member mounted adjacent an upper edge of said sloped sideface adjacent said aspiration opening for controllable movement into contact with a fragment which has not passed through said aspiration opening for applying a force to said fragment to break up that fragment and means for moving said member into contact with the fragment.

7. An apparatus as in claim 6 wherein said member is paddle shaped and pivotally mounted adjacent said aspiration opening so that pivotal movement of said member engages a fragment lodged in said aspiration opening to break up said fragment.

8. An apparatus as in claim 7 wherein said member is normally biased in an open position lying adjacent the exterior surface of said probe and further includes means manually operable outside the eye for causing pivoting of said member between said open position and a closed position to break up a fragment lodged in said aspiration opening.

9. A system for extracting a cataract comprising:
a laser for producing laser radiation to soften said cataract; and
an extracting device including a probe tube adapted for insertion into the eye through an incision and supplying an irrigation liquid to the interior of said eye through an irrigation opening and aspirating that liquid and fragments of cataract tissue through an aspiration opening, said probe having a distal insertion end and a proximal end, said distal end being shovel shaped so as to have a blunt distalmost end and a distal side face sloping from a maximum dimension to a minimum dimension at the blunt distalmost end, said aspiration opening and said irrigation opening being defined through said sloped side face, and means for dislodging fragments of tissue at said aspiration opening which have not passed through said aspiration opening.

10. A system as in claim 9 wherein said means for dislodging fragments includes means for vibrating said tube.

11. A system as in claim 9 wherein a portion of a wall of said tube adjacent said distal end and opposite to said sloped side face is roughened for polishing a posterior capsule of the eye.

12. A system as in claim 9 wherein said tube has an inner portion opening at the distal end for supplying said liquid and an outer sleeve extending about said inner portion and having at least one said aspirating opening in a wall thereof adjacent to said distal end.

13. A system as in claim 9 further including means for supplying said liquid to a first portion of said tube and means for applying a vacuum to a second portion of said tube for aspiration.

14. A system as in claim 9 wherein said laser is YAG laser.

15. A system as in claim 9 wherein said means for dislodging fragments includes a member mounted adjacent an upper edge of said sloped sideface, adjacent said aspiration opening for controllable movement into contact with a fragment which has not passed through said aspirating opening for applying a force to said fragment to break up that fragment and means for moving said member into contact with the fragment.

16. A system as in claim 15 wherein said member is paddle shaped and pivotally mounted adjacent said aspiration opening so that pivotal movement of said member engages a fragment lodged in said aspiration opening to break up said fragment.

17. A system as in claim 16 wherein said member is normally biased in an open position lying adjacent the exterior surface of said tube and further includes means manually operable outside the eye for causing pivoting of said member between said position and a closed position to break up a fragment lodged in said aspiration opening.

18. A method of extracting a cataract comprising the steps of:
focusing laser radiation onto said cataract to soften the same;
making an incision in the exterior surface of the eye;
inserting a probe through said incision to a position adjacent said cataract, said probe being adapted for insertion into the eye through an incision for supplying an irrigating liquid to the interior of said eye through an irrigation opening and aspirating that liquid and fragments of cataract tissue through an aspiration opening, said probe having a distal insertion end and a proximal end, said distal end being shovel shaped so as to have a blunt distalmost end and a distal side face sloping from a maximum dimension to a minimum dimension at the blunt distalmost end, said aspiration opening and said irrigation opening being defined through said sloped side face;
supplying an irrigation liquid to said eye via said irrigation opening in said probe;
dislodging fragments of cataract tissue from the softened cataract with the shovel shaped tip of the probe to locate such fragments adjacent said aspiration opening;
aspirating said liquid and said fragments of cataract tissue through said aspiration opening; and
dislodging fragments of cataract tissue at said aspiration opening which have not passed through said aspiration opening.

19. A method as in claim 18 including the step of polishing a posterior capsule of the eye with a roughened portion on a wall of said probe.

20. A method as in claim 18 wherein said step of making an incision includes making an incision no longer than 3.5 mm.

21. A method as in claim 18 wherein said step of dislodging at the aspiration opening includes manually causing a member pivotably mounted adjacent said aspiration opening to pivot and apply a force to said fragment which has not passed through said aspiration opening to break up that fragment.

22. A method as in claim 21 wherein said step of dislodging at the aspiration opening includes the step of vibrating said probe.

* * * * *